United States Patent [19]

Volgyesi

[11] 4,453,126
[45] Jun. 5, 1984

[54] MEASUREMENT OF ANAESTHETIC GAS CONCENTRATION

[75] Inventor: George A. Volgyesi, Toronto, Canada

[73] Assignee: The Hospital for Sick Children, Toronto, Canada

[21] Appl. No.: 24,283

[22] Filed: Mar. 26, 1979

[30] Foreign Application Priority Data

Aug. 2, 1978 [CA] Canada .................................. 308592

[51] Int. Cl.³ ...................... G01R 27/26; G01N 27/22
[52] U.S. Cl. ..................................... 324/61 R; 73/23; 324/61 P; 361/280
[58] Field of Search ........................... 324/61 P, 61 R; 23/232 E; 361/280; 73/23

[56] References Cited

U.S. PATENT DOCUMENTS 3,350,941 11/1967 Misevich et al. .................. 324/61 P
4,214,203 7/1980 Coster et al. ........................ 324/425

Primary Examiner—Ernest F. Karlsen
Attorney, Agent, or Firm—Rogers, Bereskin & Parr

[57] ABSTRACT

The invention provides a device capable of monitoring the concentration of anaesthetic gas in a breathing mixture being delivered to a patient to cause narcosis and consists essentially of an electronic transducer which provides an output signal proportional to the concentration of anaesthetic gas in a breathing mixture. The transducer includes a sensor having first and second electrical conductors positioned in proximity to one another and defining a space between the conductors. A substantially non-conductive material fills the space between the conductors and has a molecular structure which permits the absorption of the anaesthetic gas thereby causing variations in the electrical characteristics of the sensor. An electrical circuit is provided which is coupled to the sensor to provide the output signal which is proportional to the variations in the electrical characteristics of the sensor.

2 Claims, 7 Drawing Figures

MEASUREMENT OF ANAESTHETIC GAS CONCENTRATION

This invention relates to a device for monitoring the concentration of anaesthetic gas in a breathing mixture being delivered to a patient to cause narcosis.

Anaesthetic gases are delivered to a patient to cuase narcosis using carefully calibrated metering instruments. However for reasons of safety it would be preferable to monitor the concentration of these gases downstream from the valving and just before the gases are delivered to the patient. The present invention is directed towards providing a device capable of such monitoring and consists essentially of an electronic transducer which provides an output signal proportional to the concentration of anaesthetic gas in a breathing mixture. The transducer includes a sensor having first and second electrical conductors positioned in proximity to one another and defining a space between the conductors. A substantially non-conductive material fills the space between the conductors and has a molecular structure which permits the absorption of the anaesthetic gas thereby causing variations in the electrical characteristics of the sensor. An electrical circuit is provided which is coupled to the sensor to provide the output signal which is proportional to the variations in the electrical characteristics of the sensor.

The invention will be better understood with reference to the drawings in combination with the following description, and wherein.

Figure 1:
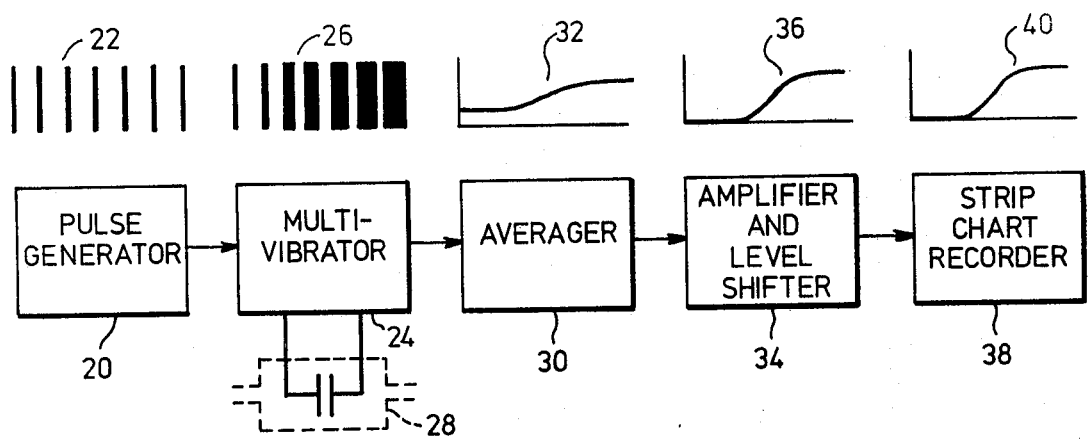
FIG. 1 is a schematic representation of a first embodiment of the invention and showing the functions of parts of the embodiment.

Reference is first made to FIG. 1 which illustrates the logic sequence of a first embodiment of the invention. Initially a pulse generator 20 provides a regular repetitive signal of constant amplitude and shown diagrammatically at 22. This signal is fed to a unistable multivibrator 24 to trigger a response for each pulse from the generator 20 resulting in an output indicated generally by the numeral 26. The output signals have a fixed amplitude and a duration dependent upon the capacitance of a sensor 28 as will be described.

Signals from the multivibrator 24 are fed to an averager 30 which effectively provides a wave form 32 reflecting the capacitance of the sensor 28. Because any point on the wave form is proportional to the concentration of anaesthetic gas at a given point in time (as will be explained), the wave form 32 must be shifted with reference to the abscissa and amplified to improve the sensitivity. This is done at an amplifier and level shifter 34 which provides a wave form 36. Preferably a strip chart recorder 38 is coupled to the output from the amplifier 34 to provide a visual readout 40.

Figure 2:
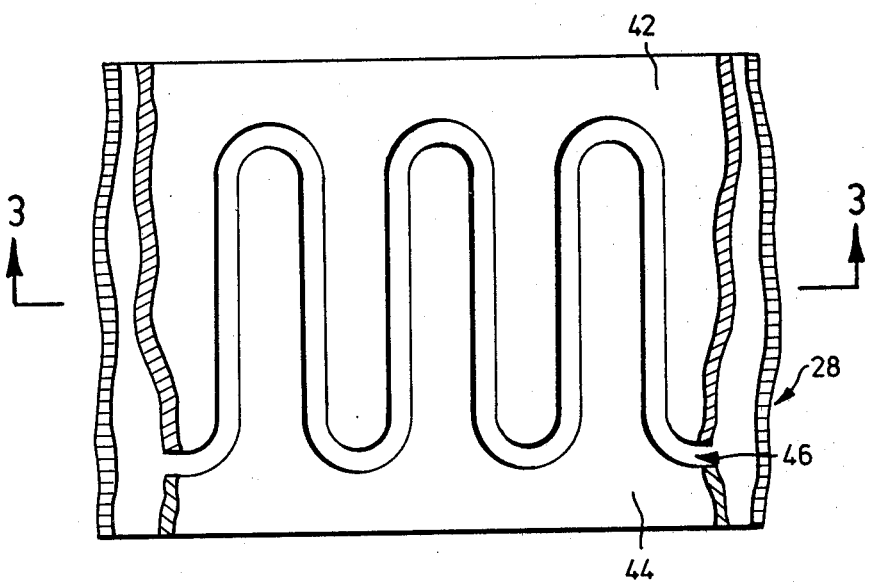
FIG. 2 is a front view of parts of the sensor during manufacture.
Figure 3:
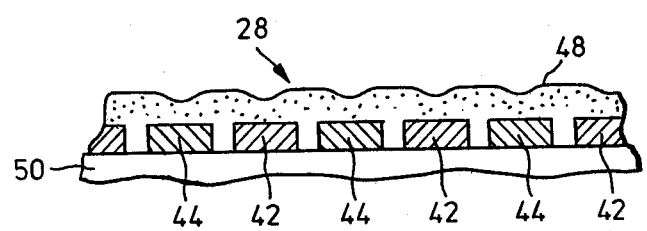
FIG. 3 is a view on line 3—3 of FIG. 2 after the sensor has been completed.

The sensor 28 must provide a signal which reflects its capacitance and which will be proportional to the concentration of anaesthetic gas in the breathing mixture. An example of a suitable sensor is shown in FIG. 2. A first electrical conductor 44 and a second electrical conductor 42 define a serpentine space 46 having constant width between the conductors. This space is then filled as shown in FIG. 3 using a material 48 having a structure capable of absorbing molecules of anaesthetic gas. It has been found that this absorption changes the electrical characteristics of the material 48 and in particular with reference to the present embodiment changes the capacitance of the sensor defined by the conductors 42, 44 and the dielectric made up of the material 48. This variation in capacitance mirrors the effect of the anaesthetic gas on the patient and consequently the anaesthetic effect can be monitored by a continuous readout of the variation of capacitance of the sensor 28.

As seen in FIG. 3, the conductive elements 42, 44 are mounted on a non-conductive and very resistive substrate 50.

Figure 4:
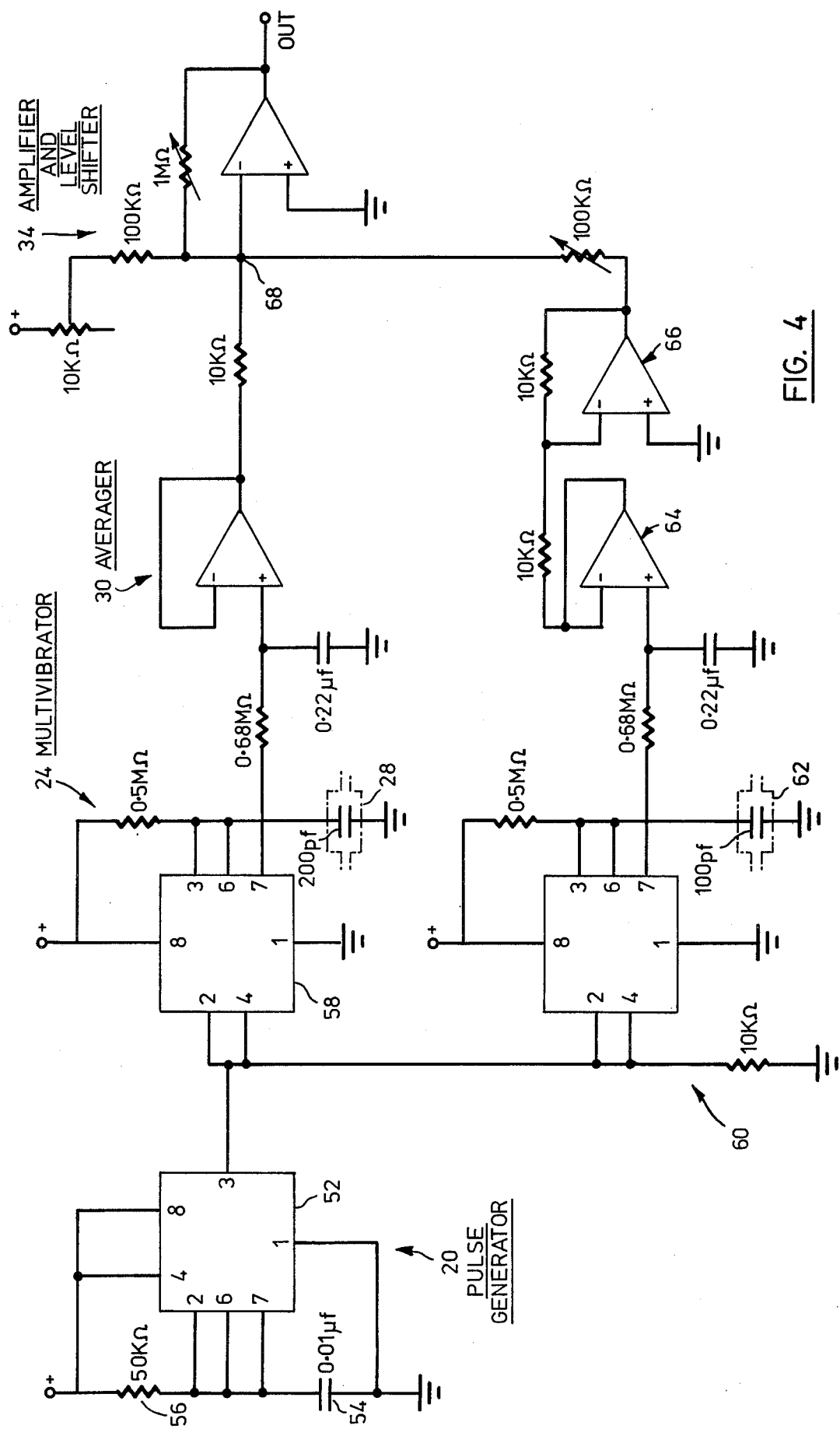
FIG. 4 is a circuit diagram of a preferred embodiment of the invention incorporating the embodiment illustrated in FIG. 1.

Before describing suitable materials for the sensor 28, the circuit diagram shown in FIG. 4 will be described. A comparison between FIG. 4 and FIG. 1 will show that the upper part of FIG. 4 corresponds to FIG. 1 without the strip chart recorder 38. The lower part of FIG. 4 will be described after those parts corresponding to FIG. 1.

The pulse generator 20 consists of a standard timer circuit NE555 shown generally by the numeral 52 and having inputs controlled by a capacitance 54 and resistor 56. This pulse generator is conventional in nature and as mentioned with reference to FIG. 1, provides a regular repeatable pulse which is fed to the multivibrator 24. This also includes a similar timer indicated generally by the numeral 58 and connected so that the output signal is dependent upon the capacitance of sensor 28. The output is pulsatile in nature and is converted by the averager 30 into a signal which is then amplified and level shifted as previously mentioned.

It is essential when delivering breathing mixture to a patient that a predetermined humidity level in the mixture be maintained. As would be expected in any capacitance circuit, an output signal is generated dependent upon the humidity in the breathing mixture. If this humidity varies at all, the output signal will be a response to both the concentration of the anaesthetic gas and to the humidity level making it impossible to obtain a useful output. In order to overcome this, a secondary circuit is provided shown at the bottom of FIG. 4. This circuit includes a multivibrator indicated generally by the numeral 60 similar to the multivibrator 24 and this is connected to a sensor 62 similar in nature to the sensor 28 but excluding the dielectric material 48 so that it is responsive only to humidity changes. Signals from the multivibrator 60 are fed to an averager shown generally by the numeral 64 and then via a signal inverter 66 to a junction 68 to sum the signals from the averager 30 and inverter 66 to effectively cancel these signals because they are opposite and equal since they both reflect humidity changes in the breathing mixture. Consequently the resulting signal at the output from this circuit depends only on the concentration of anaesthetic gas and is no longer dependent on humidity changes in the breathing mixture.

The material 48 (FIG. 3) which forms a dielectric in the sensor 28 should have a structure which permits the absorption of molecules of anaesthetic gas. Suitable materials are found in the group: lipids; and natural and synthetic elastomers. Preferably the material used is silicone rubber sold under the trade mark SILASTIC.

The conductors 42, 44 are preferably coated using a highly resistive material to eliminate conductance through the material 48. The coating can be an oxide or other suitable material.

Figure 5:
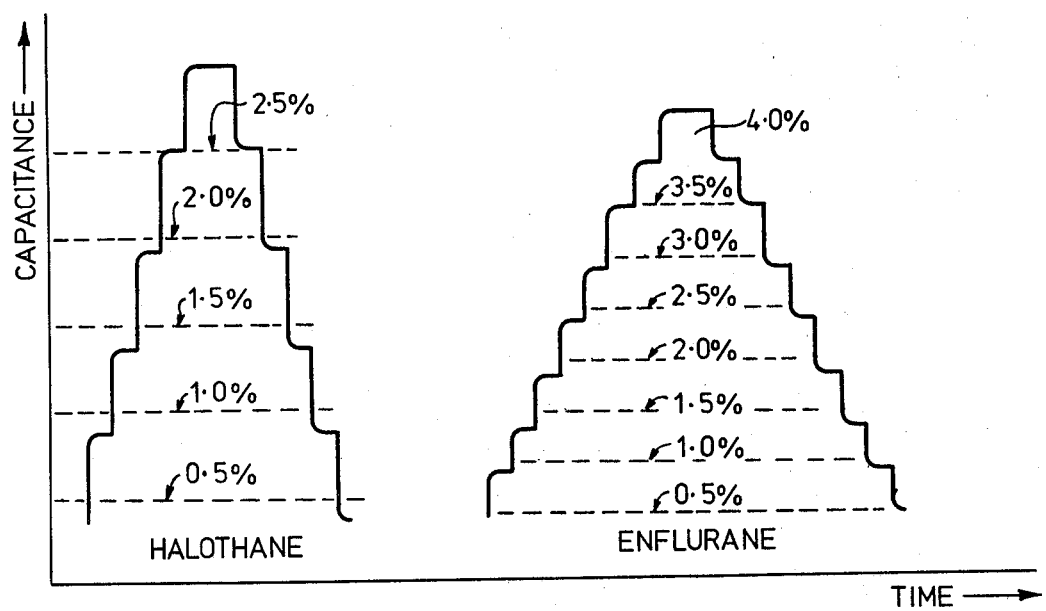
FIG. 5 illustrates results obtained using the embodiment shown in FIG. 4.

Typical results are shown in FIG. 5 for two different anaesthetic gases. It will be seen that the change in capacitance is proportional to the change in concentration of anaesthetic gas both as the anaesthetic gas concentration increases and as it decreases. It has also been found that mixtures of anaesthetic gases produce cumulative results and that the capacitance changes linearly with the effect of mixtures of anaesthetic gases.

Figure 6:
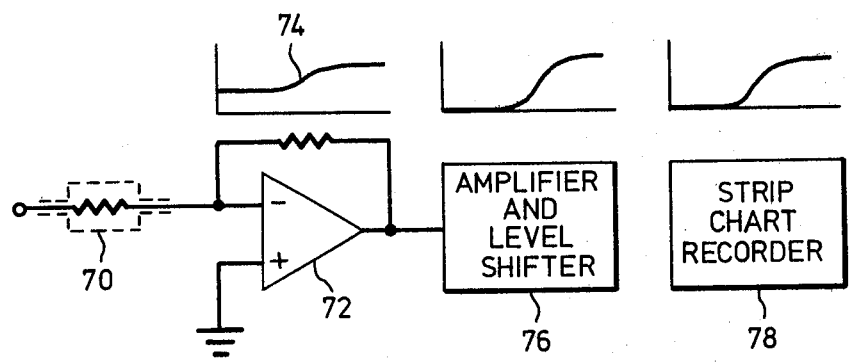
FIG. 6 is a shcematic similar to that shown in FIG. 1 and illustrating a further embodiment of the invention.
Figure 7:
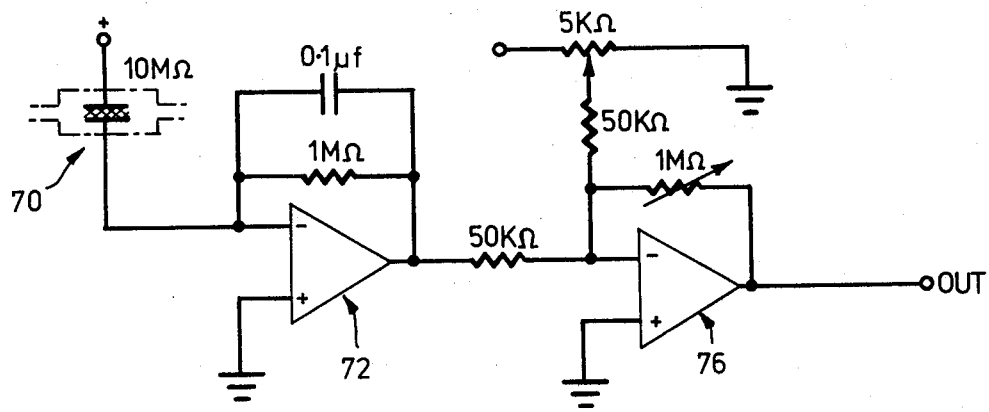
FIG. 7 is a circuit diagram of the embodiment shown in FIG. 6.

Reference is next made to FIG. 6 which illustrates an alternative embodiment of the invention. It has also been found that the materials tested can be used in a conductive mode and that the conductance of the material also varies linearly with the anaesthetic gas concentration. A simple arrangement is shown in FIG. 6 in which it will be seen that a sensor 70 is arranged in series with the input of an amplifier 72 to produce an output proportional to the conductance of the sensor 70 and indicated by the numeral 74. As before, it is necessary to provide amplification and to shift the level of the curve 74 and this is done by the amplifier and level shifter 76 before the output is fed to a strip chart recorder 78 in similar fashion to the arrangement shown in FIG. 1. To achieve these ends, a circuit such as that shown in FIG. 7 is used. Sensor 70 is positioned where anaesthetic gas can be fed past the sensor and the output from amplifier 72 is fed to the amplifier and level shifter 76 providing an output which can be fed to the chart recorder shown in FIG. 6. As was described with reference to FIG. 4, variations in signal caused by humidity changes can be accommodated using a parallel circuit similar to that shown in FIG. 4.

It will be evident from the foregoing description that the transducer of the present invention can be used either in the mode shown for sensor 28 (FIG. 4) or in the mode for sensor 70 (FIG. 7). In both cases the output signal derived is proportional to the concentration of anaesthetic gas in a breathing mixture to be fed to a patient and also, because of the simplicity of the embodiments, it is possible to provide a continuous monitoring of the breathing mixture adjacent the patient and just before the patient receives the breathing mixture. Such a safety feature is most desirable.

It will also be evident that a temperature compensating circuit can be used in a manner similar to that provided for humidity fluctuations.

I claim:

1. A transducer for providing an output signal proportional to the concentration of anaesthetic gas in a breathing mixture, the transducer comprising:

a sensor intended to be exposed to a breathing mixture containing anaesthetic gas, the sensor forming an electrical capacitor and comprising first and second electrical conductors positioned in proximity to one another and defining a space therebetween, and a substantially non-conductive material filling said space and forming a dielectric of said capacitor, the material being one of a lipid and an elastomer and having a molecular structure which permits the absorption of the anaesthetic gas and a dielectric constant which changes in proportion to changes in the concentration of said anaesthetic gas; and, electrical circuit means coupled to the sensor and adapted to provide said output signal proportional to said variations in the capacitance of the sensor.

2. A transducer as claimed in claim 1, further comprising:

a second sensor intended to be exposed to said breathing mixture and to compensate for changes in the humidity of said mixture, said second sensor forming an electrical capacitor and comprising first and second electrical conductors positioned in proximity to one another and defining a space therebetween, said second sensor being connected in said electrical circuit means, and said electrical circuit means being adapted to modify said output signal to compensate for changes in the humidity of the breathing mixture detected by said second sensor.

* * * * *